(12) United States Patent
Zhang et al.

(10) Patent No.: US 11,389,084 B2
(45) Date of Patent: Jul. 19, 2022

(54) ELECTRONIC DEVICE AND METHOD OF CONTROLLING SAME

(71) Applicant: Georgia Tech Research Corporation, Atlanta, GA (US)

(72) Inventors: Cheng Zhang, Atlanta, GA (US); Gregory D. Abowd, Atlanta, GA (US); Omer Inan, Atlanta, GA (US); Thad Eugene Starner, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 399 days.

(21) Appl. No.: 16/325,932

(22) PCT Filed: Aug. 15, 2017

(86) PCT No.: PCT/US2017/046960
§ 371 (c)(1),
(2) Date: Feb. 15, 2019

(87) PCT Pub. No.: WO2018/035129
PCT Pub. Date: Feb. 22, 2018

(65) Prior Publication Data
US 2019/0175077 A1    Jun. 13, 2019

Related U.S. Application Data

(60) Provisional application No. 62/374,939, filed on Aug. 15, 2016.

(51) Int. Cl.
*A61B 5/11* (2006.01)
*A61B 5/00* (2006.01)
(Continued)

(52) U.S. Cl.
CPC ............ *A61B 5/1123* (2013.01); *A61B 5/681* (2013.01); *A61B 5/7257* (2013.01);
(Continued)

(58) Field of Classification Search
CPC ... A61B 5/1121; A61B 5/1122; A61B 5/1123; A61B 5/681; A61B 5/6824;
(Continued)

(56) References Cited

U.S. PATENT DOCUMENTS

| 8,624,836 B1 | 1/2014 | Miller |
| 2014/0282270 A1 | 9/2014 | Slonneger |

(Continued)

FOREIGN PATENT DOCUMENTS

| CN | 103760970 | 4/2014 |
| CN | 105022471 | 11/2015 |

(Continued)

OTHER PUBLICATIONS

International Search Report and Written Opinion from PCT Application No. PCT/US17/46960 dated Oct. 31, 2017 (21 pages).

(Continued)

*Primary Examiner* — Aaron F Roane
(74) *Attorney, Agent, or Firm* — Troutman Pepper Hamilton Sanders LLP (57) ABSTRACT

A portable electronic device including: a plurality of sensors configured to generate, in response to a first contact with a body of a user in a vicinity of the portable electronic device, one or more first input signals; a microprocessor; and a memory having stored thereon instructions that, when executed by the microprocessor, control the microprocessor to execute, in response to an analysis of the one or more first input signals indicating that the first contact corresponds to a first gesture, and by the microprocessor, a first command corresponding to the first gesture.

49 Claims, 7 Drawing Sheets

(51) Int. Cl.
*G06F 1/16* (2006.01)
*G06F 3/043* (2006.01)
*G06F 3/04886* (2022.01)
*G06F 3/0346* (2013.01)

(52) U.S. Cl.
CPC .......... *A61B 5/7264* (2013.01); *A61B 5/7267* (2013.01); *A61B 5/7475* (2013.01); *G06F 1/163* (2013.01); *G06F 3/0346* (2013.01); *G06F 3/0433* (2013.01); *G06F 3/04886* (2013.01); *A61B 2562/0219* (2013.01)

(58) Field of Classification Search
CPC ... A61B 5/6825; A61B 5/7257; A61B 5/7264; A61B 5/7267; A61B 5/7275; A61B 5/7282; A61B 2562/0219; G06F 1/163; G06F 3/0346; G06F 3/0433; G06F 3/04886
USPC ........................................................ 600/301
See application file for complete search history.

(56) References Cited

U.S. PATENT DOCUMENTS

| 2015/0160731 | A1  | 6/2015  | Yun et al.    |             |
|--------------|-----|---------|---------------|-------------|
| 2015/0286285 | A1* | 10/2015 | Pantelopoulos | A61B 5/6824 |
|              |     |         |               | 345/156     |
| 2015/0317076 | A1* | 11/2015 | Goel          | G06F 3/04186 |
|              |     |         |               | 345/173     |
| 2016/0073073 | A1* | 3/2016  | Ha            | G03B 29/00  |
|              |     |         |               | 345/156     |
| 2016/0091980 | A1  | 3/2016  | Baranski et al. |           |
| 2018/0164892 | A1* | 6/2018  | Han           | G06F 3/0346 |
| 2021/0323521 | A1  | 10/2021 | Lee et al.    |             |

FOREIGN PATENT DOCUMENTS

| CN | 105183345     | 12/2015 |
| CN | 105706024     | 6/2016  |
| WO | 2011/068632 A2 | 6/2011 |
| WO | 2015/060856   | 4/2015  |

OTHER PUBLICATIONS

Office Acton from Chinese Patent Application No. 2017800576588 dated Jun. 3, 2021.
Search Report from Chinese Patent Application No. 2017800576588 dated May 30, 2021.
Extended European Search Report and Written Opinion from EP Application No. 17841995.8, dated Feb. 14, 2020.
Examination Report from EP Application No. 17841995.8 dated Jun. 15, 2021.

* cited by examiner

ELECTRONIC DEVICE AND METHOD OF CONTROLLING SAME

CROSS-REFERENCE TO RELATED APPLICATIONS

This application claims priority to U.S. Provisional Patent Application No. 62/374,939 filed Aug. 15, 2016, the disclosure of which is incorporated herein by reference in its entirety.

BACKGROUND

1. Field

The present disclosure relates generally to portable electronic devices, and more particularly to providing user commands to portable electronic devices by non-traditional means.

2. Description of Related Art

Many portable electronic devices, by necessity, are relatively small compared to traditional computing devices. Input technologies for traditional personal computing devices cannot be easily replicated on portable devices because of this size and form factor disparity. The size and form factor disparity even greater for most wearable electronic devices, such as a smart watch.

A smart watch, for example, uses a built-in capacitive multi-touch screen as a surface for both user input and output display. Unfortunately, the small size of the smart watch screen compared to traditional personal computing devices limits the richness of user interactions with the smart watch. Many successful interactions on smart phones, including some multi-touch gestures, cannot be reproduced on a smart watch. Interaction issues, such as a finger occluding portions of the screen, may seem insignificant on a smart phone, but are exaggerated on a smart watch.

Prior attempts to expand the capabilities of wearable electronic devices to detect and respond to an increased variety of human interactions have required the use of additional hardware, such as wearable keyboards, or instrumenting the body with sensors. While such solutions may increase the variety of human interactions, additional equipment, internal or external, add bulk and complexity to the wearable device, negatively affecting the convenience of the wearable electronic device.

There is therefore a need to expand the capabilities of wearable electronic devices to detect and respond to an increased variety of human interactions without the use of additional input equipment.

SUMMARY

Briefly described, in an example form, certain embodiments include a wearable electronic device including: a plurality of sensors configured to generate, in response to a first contact with a body of a user in a vicinity of the wearable electronic device, one or more first input signals; a microprocessor; and a memory having stored thereon instructions that, when executed by the microprocessor, control the microprocessor to execute, in response to an analysis of the one or more first input signals indicating that the first contact corresponds to a first gesture, and by the microprocessor, a first command corresponding to the first gesture.

The wearable electronic device may be a wrist-mounted device.

The first gesture may be a tap or a swipe performed on a hand or forearm of the user in the vicinity of the wearable electronic device.

The plurality of sensors may be configured to generate, in response to a second contact with the body of the user in the vicinity of the wearable electronic device, one or more second input signals, and the instructions may further control the microprocessor to execute, in response to an analysis of the one or more second input signals indicating that the second contact corresponds to a second gesture, by the microprocessor, a second command corresponding to the second gesture.

The first command and the second command may be distinct commands mapped to the first gesture and the second gesture, respectively.

The first command executed by the microprocessor may control the wearable electronic device to respond to the first gesture by providing a feedback to the user.

The first contact may be provided by direct skin-to-skin contact. The direct skin-to-skin contact may consist of a finger contacting a location of skin near the vicinity of the wearable electronic device.

The contact may be a tap, a swipe, or a double tap.

The plurality of sensors may include an accelerometer, a gyroscope, and a microphone.

The receiving one or more first input signals may include receiving an acceleration signal from the accelerometer, receiving a rotational movement signal from the gyroscope, and receiving an acoustic waveform signal from the microphone.

The first gesture may be one of a plurality of gestures in a gesture family, each of the plurality of gestures in the gesture family being mapped to one of a plurality of commands, and the first command being one of the plurality of commands.

The gesture family may consist of 5 or more gestures.

The wearable electronic device may be a wrist-mounted device, and the gesture family may include 10 gestures corresponding to a number pad on the back of the hand.

The first gesture may include a tap to a back of a forearm of the user in the vicinity of the wearable electronic device, and the first command may instruct the microprocessor to begin or cease monitoring for one or more other gestures in the gesture family.

The instructions may further control the microprocessor to analyze the one or more input signals to determine that the first contact corresponds to the first gesture.

The analysis may include gesture event detection and gesture classification.

The gesture classification may be based, at least in part, on user-dependent gesture event data.

The gesture event detection may include context detection.

The instructions may further control the microprocessor to analyze one or more second input signals generated by the plurality of sensors to determine that the one or more second input signals do not correspond to a gesture in a gesture family detectable by the wearable electronic device.

According to some embodiments, there is provided a method including: capturing, in response to a contact to the body of a user in a vicinity of a wearable electronic device, first sensor data from one or more sensors integral to the wearable electronic device; and providing, in response to an analysis of the first sensor data indicating that the contact corresponds to a first gesture, a first command to a microprocessor of the wearable electronic device.

The method may further include analyzing first the sensor data.

Analyzing the first sensor data may include performing gesture event detection and performing gesture classification.

Gesture event detection may include comparing a peak value from the first sensor data to a threshold value.

Gesture event detection may include determining a motion of the user.

The motion of the user may be a walking motion, and gesture event detection may further include compensating for the effect of the walking motion on the first sensor data.

Gesture classification may include extracting a plurality of features from the first sensor data, generating an event vector based on the plurality of features, and comparing the event vector to a plurality of gesture classification models.

The plurality of gesture classification models may include user-independent models.

The plurality of gesture classification models may be based, at least in part, on a plurality of contacts to the body of a user in the vicinity of the wearable electronic device, each of the plurality of contacts corresponding to one of a plurality of gestures in a gesture family.

The plurality of gestures in a gesture family may represent a ten-key number pad.

The first sensor data may include an acceleration signal, a rotational movement signal, and an acoustic waveform signal.

The method may further include analyzing the first sensor data, the analyzing including extracting a plurality of features from the first sensor data.

The extracting of the plurality of features may include performing a time-based derivative and calculating statistical parameters of the acceleration signal, performing a Fast Fourier Transform on the rotational movement signal, and performing a Fast Fourier Transform on the acoustic waveform signal.

The analyzing may further include generating an event vector based on the plurality of features.

The analyzing may further include comparing the event vector to a plurality of gesture classification models.

The first gesture may be a tap, a swipe, or a double tap.

The first gesture may be one of a plurality of gestures in a gesture family. Each of the plurality of gestures in the gesture family may be mapped to one of a plurality of commands, and the first command may be one of the plurality of commands.

The wearable electronic device may be a wrist-mounted device.

The contact may be a tap, a swipe, or a double tap of a finger to the back of a hand or a forearm.

The contact may be direct skin-to-skin contact.

The gesture family may consist of 5 or more gestures.

The gesture family may include ten gestures corresponding to a number pad on the back of the hand.

The first gesture may include a tap to a back of the forearm, and wherein the first command instructs the microprocessor to begin or cease monitoring for one or more other gestures in the gesture family.

The method may further include providing, based on the first command provided to the microprocessor, feedback to the user.

The feedback to the user may include a text or number entry displayed on a screen of the wearable electronic device, a selection of a menu item displayed on the screen, or the selection of a button displayed on the screen.

Gesture event detection may include determining an event window that includes gesture event data.

The method may further include: capturing second sensor data from one or more sensors integral to the wearable electronic device; and analyzing the second sensor data to determine that the second sensor data does not correspond to a gesture in a gesture family detectable by the wearable electronic device.

According to some embodiments, there is provided a method including: capturing, in response to a contact to the body of a user in a vicinity of a portable electronic device, sensor data from one or more sensors integral to the portable electronic device; and providing, in response to an analysis of the sensor data indicating that the contact corresponds to a first gesture, a first command to a microprocessor of the portable electronic device.

The method may further include analyzing the sensor data.

Analyzing the sensor data may include performing gesture event detection and performing gesture classification.

Gesture event detection may include comparing a peak value from the sensor data to a threshold value.

Gesture event detection may include determining a motion of the user.

The motion of the user may be a walking motion, and gesture event detection may further include compensating for the effect of the walking motion on the sensor data.

Gesture classification may include extracting a plurality of features from the sensor data, generating an event vector based on the plurality of features, and comparing the event vector to a plurality of gesture classification models.

Gesture classification models may be user-independent models.

The plurality of gesture classification models may be based, at least in part, on a plurality of contacts to the body of a user in the vicinity of the portable electronic device, each of the plurality of contacts corresponding to one of a plurality of gestures in a gesture family.

The plurality of gestures may represent a ten-key number pad.

Sensor data may include an acceleration signal, a rotational movement signal, and an acoustic waveform signal.

The extracting of the plurality of features may include performing a time-based derivative and calculating statistical parameters of the acceleration signal, performing a Fast Fourier Transform on the rotational movement signal, and performing a Fast Fourier Transform on the acoustic waveform signal.

The first gesture may be a tap, a swipe, or a double tap.

The first gesture may be one of a plurality of gestures in a gesture family, where each of the plurality of gestures in the gesture family is mapped to one of a plurality of commands, and the first command is one of the plurality of commands.

The portable electronic device may be held in the hand of the user and the contact to the body may be in the vicinity of the hand of the user.

The contact to the body may be a tap, swipe, or a double tap of a finger to the back of a hand or a forearm.

The contact may be direct skin-to-skin contact.

The gesture family may consist of 5 or more gestures.

The gesture family may include ten gestures corresponding to a number pad on the back of the hand.

The first gesture may comprise a tap to a forearm of the same arm attached to the hand of the user holding the portable electronic device, and the first command may instruct the microprocessor to being or cease monitoring for one or more other gestures in the gesture family.

The method may further include providing, based on the first command provided to the microprocessor, feedback to the user.

The feedback to the user includes a text or number entry displayed on a screen of the portable electronic device, a selection of a menu item displayed on the screen, or the selection of a button displayed on the screen.

Gesture event detection may include determining an event window that includes gesture event data.

The method may further include: capturing second sensor data from one or more sensors integral to the portable electronic device; and analyzing the second sensor data to determine that the second sensor data does not correspond to a gesture in a gesture family detectable by the portable electronic device.

According to some embodiments, there may be provided a non-transitory computer readable medium having stored thereon computer program code that, when executed by a processor, controls a processor to perform one or more of the above described methods.

DETAILED DESCRIPTION

To facilitate an understanding of the principles and features of the various embodiments of the invention, various illustrative embodiments are explained below. Although example embodiments are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the example embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the certain example embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" or "substantially" one particular value and/or to "about" or "approximately" or "substantially" another particular value. When such a range is expressed, other example embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of certain embodiments are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

1. Overview

Various example embodiments of a wearable electronic device and methods to be used with the wearable electronic device are presented. Embodiments utilize the body of the user in the vicinity of the wearable electronic device as a surface for providing user input to the wearable electronic device. By extending the user input surface outward, for example to the skin, the user can view the screen of the wearable electronic device while interacting with the wearable electronic device, similar to the indirect user interaction provided by a track pad of a portable computer.

Figure 1:
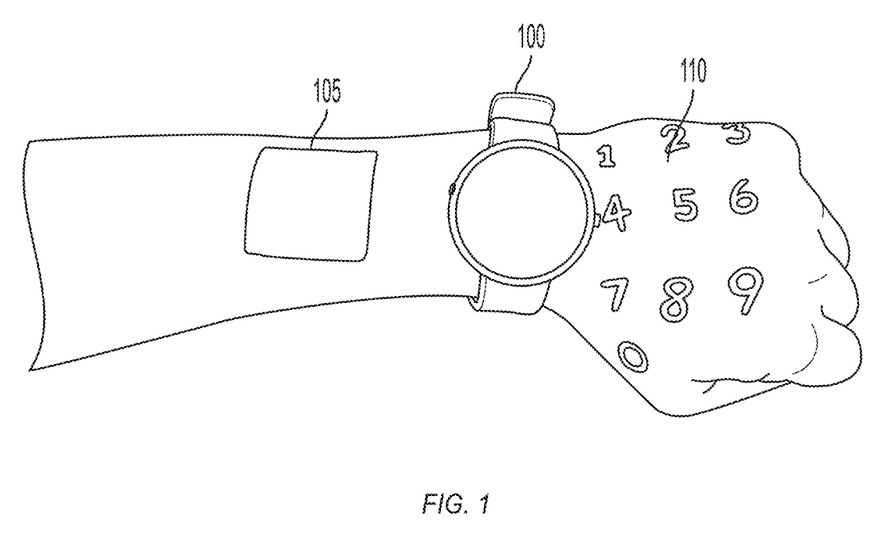
FIG. 1 illustrates a wearable electronic device according to an example embodiment.

The described embodiments utilize direct contact with the body without the need for additional hardware or sensors external to the wearable electronic device. FIG. 1 illustrates a wearable electronic device 100 according to an embodiment. The depicted wearable electronic device 100 is a smart watch worn on the wrist of a user. As will be appreciated and understood, certain aspects of the present disclosure may be used with a variety of wearable electronic devices such as smart glasses, activity trackers, wearable cameras, health monitors, etc. wherein the wearable electronic device is worn at various locations on the body such as the head, chest, upper arm, torso, foot, lower leg, or thigh, for example.

In the example embodiment illustrated in FIG. 1, the skin of the user near the wearable electronic device 100 has a one touch region 105 and a keypad region 110. According to certain aspects of the example embodiment, the keypad region 110 can provide input to the wearable electronic device 100 at up to 10 tap locations. The keypad region 110 can provide input to the wearable electronic device 100 using four slide gestures. The one touch region 105 according to the example embodiment can provide a single tap input; however, other embodiments can make use of a wider range of inputs to the forearm region. The depicted example embodiment of FIG. 1 is therefore capable of providing up to 15 distinct inputs. The set of 15 distinct gesture inputs represent one possible gesture family according to the illustrated example embodiment; however, this is merely an example, and the range of gesture inputs can be extended to include an even richer input language, allowing for textual and other inputs.

Figure 2A:
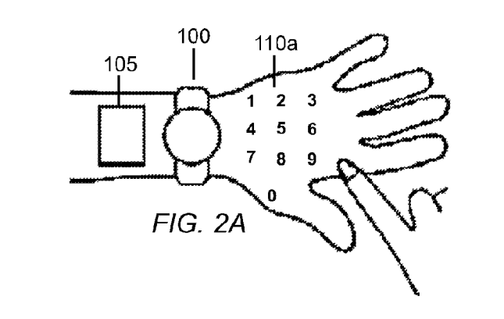
FIGS. 2A, 2B, 2C, and 2D illustrate possible gesture families according to example embodiments.
Figure 2B:
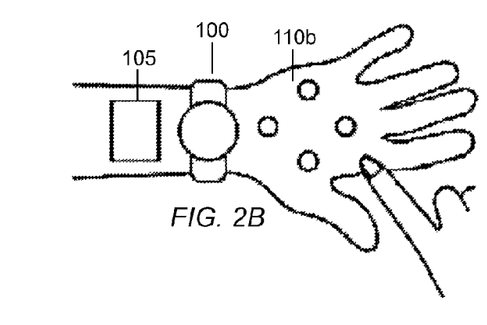
Figure 2C:
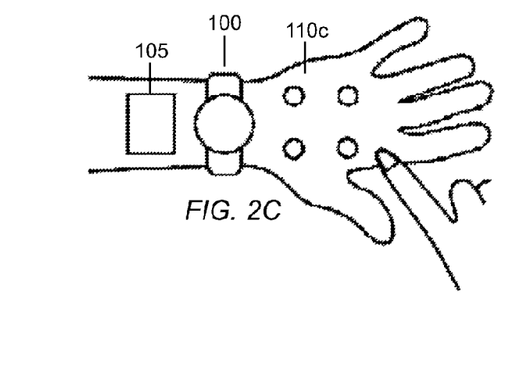

As shown in FIG. 1 and FIG. 2A, the keypad region 110 may include a number pad (NumPad) 110a. As shown in FIG. 2B, the keypad region 110 may include a DPad 110b, or as shown in FIG. 2C, the keypad region 110 may include a CornerPad 110c. Up, down, left, and right swipe gestures 110d illustrated in FIG. 2D may also be input on the keypad region 110.

The NumPad 110a gesture family simulates the layout of a number pad, which provides 10 distinct tap locations in the keypad region 110. The NumPad 110a gesture family can potentially be used for entering numbers or even text (through multi-tap such as Twiddler or T9), which is currently difficult on a small touch screen. The one touch region 105 can serve a variety of functions. For example, gesturing (including tapping) on the one touch region 105 can serve as the activation gesture, informing the wearable electronic device as to when it should be receptive to inputs from the keypad region 110. Gesturing on the one touch region 105 can be interpreted as an undo command. In some cases, the commands corresponding to gestures within a gesture family may be context specific, and may change based on a current state of the wearable electronic device 100 (e.g., receiving a telephone call, playing a game, etc.).

As shown in FIG. 2B, the keypad region 110 may include a DPad 110b gesture family having four tap locations forming a diamond shape with top, bottom, left, and right locations. The DPad 110b can be useful for directional controls or scrolling through a list of items. For example, scrolling down a menu vertically or horizontally, are common operations on a smart watch touch screen. The one touch region 105 can be used to input an activation gesture or a selection gesture to confirm the selection of a menu item. For applications that display a lot of information, the DPad 110b can reduce screen occlusion while providing an intuitive means for interaction with the wearable electronic device 100.

As shown in FIG. 2C, the keypad region 110 may include a CornerPad 110c gesture family having four tap locations forming a square shape with two tap locations above and below each other close to the wearable electronic device 100 (e.g. near the wrist on the back of a hand) and two tap locations above and below each other further from the wearable electronic device 100 (e.g. near the knuckles at the base of two fingers on the back of a hand). The CornerPad 110c can be used as shortcuts to certain applications on a wearable electronic device (such as a smart watch) 100. The one touch region 105 can be used to input an activation gesture to activate the CornerPad 110c input functionality.

Figure 2D:
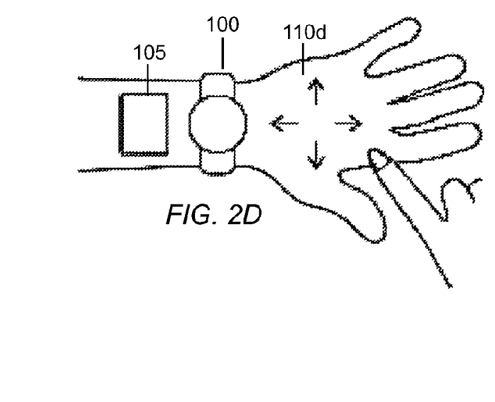
Figure 3A:
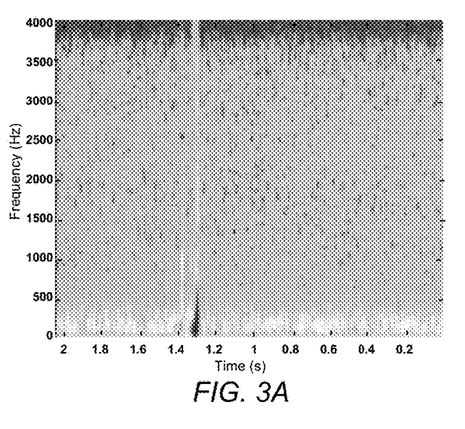
FIGS. 3A, 3B, 3C, and 3D each depict a spectrograph of the acoustic signal of a microphone recording of a tap gesture according to an example embodiment.
Figure 3B:
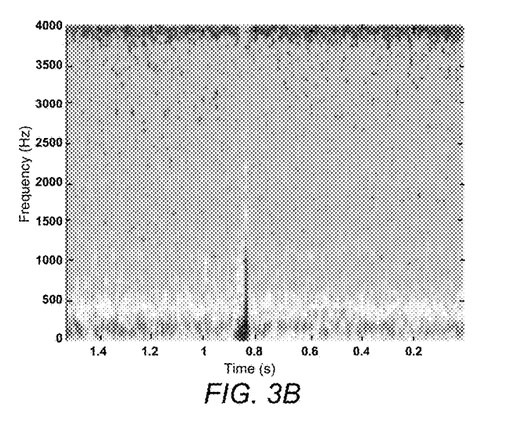
Figure 3C:
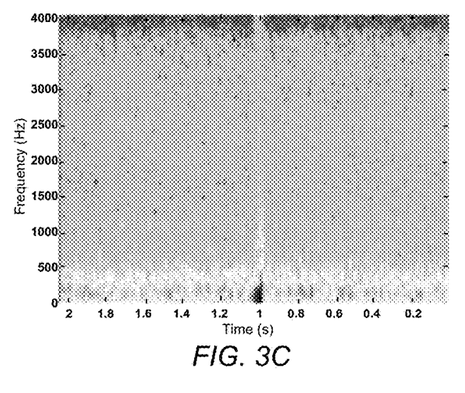
Figure 3D:
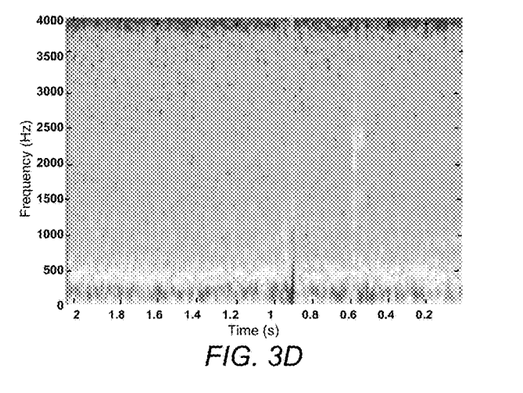
Figure 4A:
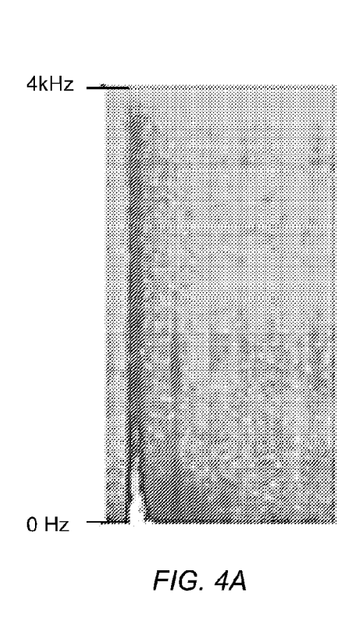
FIGS. 4A, 4B, 4C, and 4D each depict a spectrograph of the acoustic signal of a microphone recording of a tap gesture (FIGS. 4A and 4B) or a swipe gesture (FIGS. 4C and 4D) according to an example embodiment.
Figure 4B:
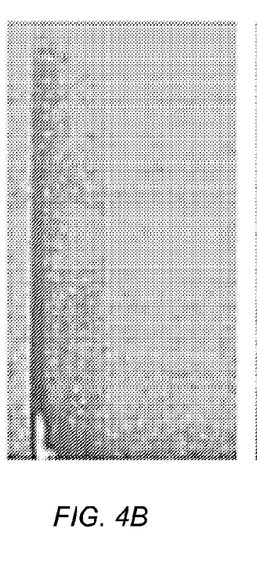
Figure 4C:
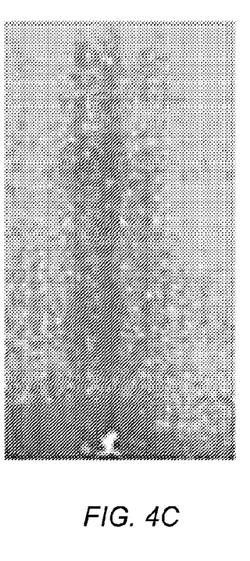
Figure 4D:
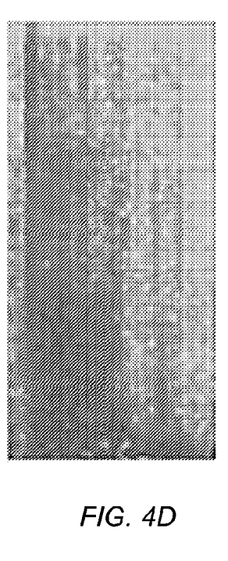

As shown in FIG. 2D, up, down, left and right swipe gestures 110d may be input at the keypad region 110. A diamond shaped keypad, such as DPad 110b may be useful in mapping the up, down, left, and right swipe gestures 110d.

As will be appreciated and understood, tap locations and sliding gestures are not limited to the locations depicted in FIG. 1 or FIGS. 2A through 2D. Tap locations may include other locations that are in the vicinity of the wearable electronic device. Sliding gestures may be performed in other directions or at other locations in the vicinity of the wearable electronic device. For example a wearable electronic device worn on the upper arm or torso may receive input from a gesture family that includes taps and sliding gestures in the vicinity of those respective locations.

Some embodiments of the wearable electronic device 100 can include sensors integrated into the wearable electronic device such as an inertial measurement unit (IMU). The IMU may include an accelerometer, a gyroscope, or both. Such embodiments can be configured to detect and distinguish taps at various tap locations by using the IMU. Such embodiments can further include a microphone and can be configured to detect and distinguish taps at various tap locations by using the IMU and microphone. Embodiments including an IMU or an IMU and a microphone can be configured to detect and distinguish a family of on-body gestures including sliding gestures in addition to or in place of taps.

Some embodiments may utilize user-dependent models, user-independent models, user adaptive models, or a combination thereof to detect and distinguish a family of on-body gestures including taps at various tap locations.

2. Demonstrations—Sensor Data Collection

To illustrate possible implementations of the wearable electronic device technology, the functionality according to aspects of some embodiments were implemented on a Sony SmartWatch3 and a Motorola Moto 360. Implementations utilized sensor data from the gyroscope, accelerometer, and microphone of the SmartWatch3 and the Moto 360. It will be understood that these example implementations are for illustrative purposes only, and any specified elements (e.g., accuracy and precision), are for the edification of one of ordinary skill only, and are not to be taken as representative of all embodiments within the scope of the present disclosure.

Implementations using the SmartWatch3 utilized the one touch region 105 and various tap location configurations in the keypad region 110 such as NumPad 110a, DPad 110b, and CornerPad 110c. Implementations using the Moto 360 utilized slide gestures 110d in addition to touch inputs.

Taps or gestures on the body generate sound that propagates from the point of contact to the microphone in the smart watch. The microphone converts the sound into an electrical signal that can be characterized by the energy of the signal over a range of frequencies as a function of time. FIGS. 3A, 3B, 3C, and 3D depict graphs of acoustic signals received by the microphone of the SmartWatch3 when tapping numbers 1, 3, 7, and 9 respectively on the keypad region 110 at NumPad 110a tap locations. Comparing FIG. 3B to FIG. 3A, tapping on the number 3 can have more energy at lower frequencies compared to tapping on the number 1. This is because of the thickness of the tissue, the ratio of fat, and the structure of the bone are different at different locations on the back of the hand and on the top of the forearm. For instance, the position of number 3 is closer to the knuckle, which has more bone compared to position of number 1.

FIGS. 4A, 4B, 4C, and 4D depict graphs of characterized electrical signals based on sound received by the microphone of the Moto 360 when tapping number 2, tapping number 9, sliding down, and sliding right on the keypad region 110. As shown in the graphs in FIGS. 3A through 3D and FIGS. 4A through 4D, sounds produced by sliding or tapping on the skin of the back of the hand and forearm fell between 0 Hz and 4 kHz. The sound from the microphones on the SmartWatch3 and the Moto 360 were down-sampled to 8 kHz in the presented implementations to make data collection effective but practical. As would be appreciated and understood, sound from the microphones may be sampled at a higher sample rate to capture a broader range of sound frequencies.

Figure 5A:
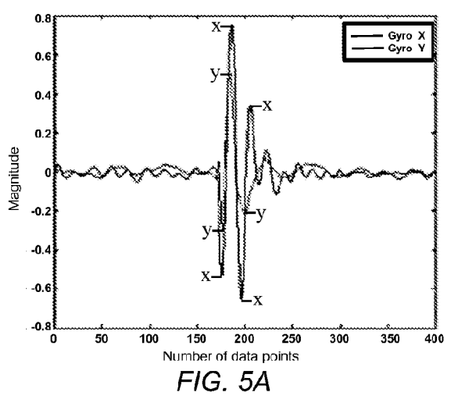
FIGS. 5A, 5B, 5C, and 5D each depict the magnitude of an x-axis signal and a y-axis signal generated by a gyroscope in response to a tap gesture according to an example embodiment.
Figure 5B:
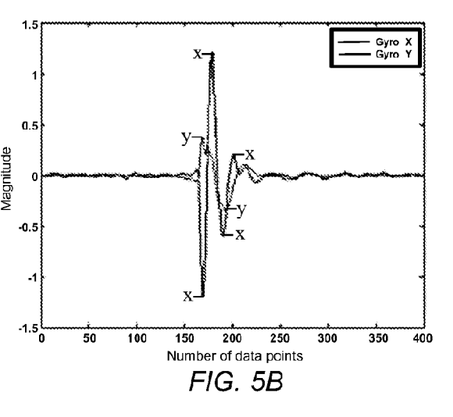
Figure 5C:
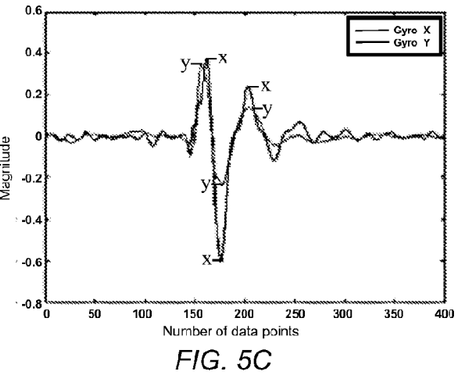
Figure 5D:
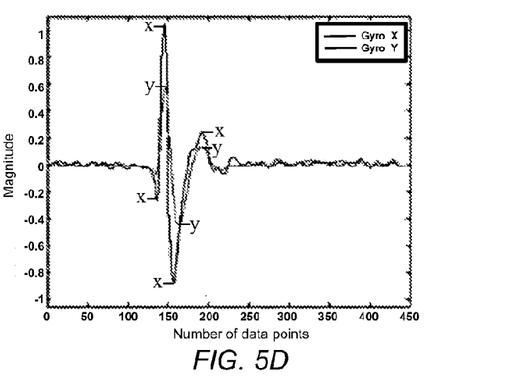
Figure 6:
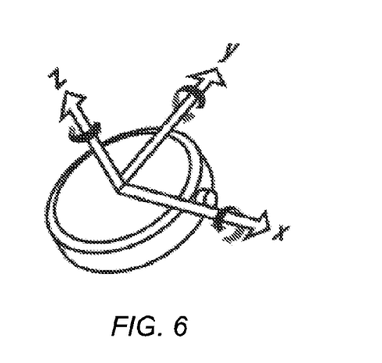
FIG. 6 illustrates the axes of rotation of a wearable electronic device according to an example embodiment.

Taps or gestures on the body induce movement of the arm that the smart watch is mounted on. Movement of the arm may be detected by the gyroscope. Data from the gyroscope can be characterized as a magnitude of motion in the x, y, or z directions (or some combination thereof) as a function of time. FIG. 6 depicts the orientation of motion in the x, y, and z directions for wrist-mounted devices such as smart watches. FIGS. 5A, 5B, 5C, and 5D depict graphs of characterized gyroscope data from the SmartWatch3 based on motion of the arm when tapping numbers 1, 3, 7, and 9 respectively on the keypad region 110 NumPad 110a. Tapping on different locations on the back of the hand introduces different kinds of movement. For instance, as shown in FIG. 5C or FIG. 5D, tapping numbers 7 or 9 resulted in first a positive peak in the magnitude of motion on the x-axis of the gyroscope and then a negative peak. In comparison, as shown in FIG. 5A or FIG. 5B, tapping numbers 1 or 3 resulted in first a negative peak and then a positive peak in the magnitude of motion on the y-axis of the gyroscope.

Although gyroscope signals from the x and y-axis are presented and discussed, signals from any axis of the gyroscope or the accelerometer, or a combination thereof can be utilized in determining if a gesture event has occurred or classifying a gesture.

For implementations utilizing the SmartWatch3, the gyroscope was sampled at the highest sampling rate available (200 Hz). For implementations utilizing the Moto 360, the gyroscope was sampled at 50 Hz. As would be appreciated and understood, the gyroscope could be sampled at rates less than 50 Hz and up to the physical limitations of the wearable device to capture the desired frequency range of rotational movement.

Implementations utilized linear acceleration data (excluding acceleration due to gravity) instead of raw accelerator data to prevent the orientation of the wrist from influencing the gesture recognition results, although raw acceleration data could be utilized in other embodiments and implementations. For implementations utilizing the SmartWatch3 and the Moto 360, the accelerometer was sampled at 250 Hz and 25 Hz respectively. As would be appreciated and understood, the accelerometer could be sampled at rates up to the physical limitations of the wearable device to capture the desired frequency range of changes in acceleration.

3. Demonstrations—Data Capture and Analysis

Figure 7:
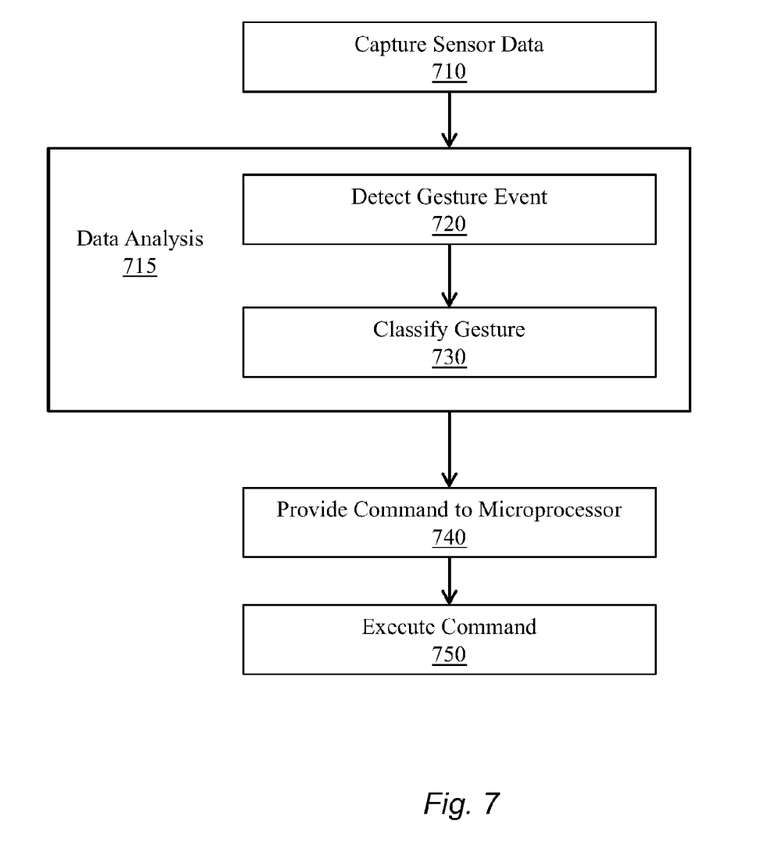
FIG. 7 illustrates a method for controlling a portable or wearable electronic device according to an example embodiment.

FIG. 7 illustrates methods to be used with the wearable electronic device according to some example embodiments. The method can include the steps of capturing sensor data 710, analyzing the sensor data 715, providing a command to a microprocessor 740, and executing the command 750.

According to some embodiments, sensor data can be captured and recorded for later analysis or captured and analyzed in real time. Sensor data can include data from sensors of the wearable electronic device as described above. By way of example and not limitation, a sliding window can be applied to the sensor data, and data contained within the sliding window can proceed to the data analysis 715. The data analysis may be performed, as non-limiting examples, by the wearable electronic device or some other device in communication with the wearable electronic device. For example, the wearable electronic device may be in wireless communication with a phone, and may transmit the captured sensor data 710 (raw or processed) to the phone for data analysis.

According to some embodiments, the data analysis 715 can include a machine learning pipeline including: (1) gesture event detection 720 and (2) gesture classification 730. Gesture event detection 720 identifies the presence of sensor data that can be an indicator that a user has input a gesture. During gesture even detection 720, a motion of a user not related to inputting a gesture may be compensated for by, for example, applying a high pass filter to the sensor data. For example, motion of a user walking may be compensated for. The sensor data can be compared to a threshold value or values. A threshold value (or values) could be compared to data from one sensor or a combination of sensors. An event window containing data related to a user potentially inputting a gesture can be located, for example at a temporal location where the sensor data exceeds a threshold value such the event window includes a time period that corresponds to a user inputting a gesture.

The gesture classification 730 classifies the detected gesture event as a gesture, such as, by way of example and not limitation, one of the described above with reference to FIGS. 2A-2D. Gesture classification 730 can include extracting features from sensor data, generating an event vector, comparing the event vector to gesture classification models, and classifying the gesture event into a gesture family. In some cases, gesture classification may serve as a secondary check to determine whether a user has inputted a gesture. For example, the threshold value for gesture event detection 720 may be low enough to allow false positives (e.g., detecting a gesture during an event window where one did not occur); gesture classification 730 may determine whether the "detected" potential gesture is a false positive or corresponds to a gesture in a gesture family.

The classified gesture may correspond to a command to a microprocessor. The command can be provided to the microprocessor 740 in response to the gesture input on the body of the user. The command can then be executed 750. In some cases, the command may be context dependent (e.g., based on a state of the wearable electronic device or an application executing on the wearable electronic device). As a non-limiting example, the wearable electronic device may provide feedback to the user.

For the example implementation utilizing the SmartWatch3, during gesture event detection 720, a moving gesture detection window of 1.2 second duration with 75% overlap was applied to two-second raw data streams recorded from the gyroscope, accelerometer, and microphone. As will be appreciated and understood, a moving gesture detection window may have a longer or shorter duration and a longer or shorter overlap in order to effectively capture gesture inputs.

In the example implementation utilizing the SmartWatch3, the rotational movement data from the gyroscope and linear acceleration data from the accelerometer was analyzed to determine if the data passed an empirically determined threshold value at any point in the gesture detection window. As would be appreciated and understood, threshold values could be determined for the accelerometer and gyroscope individually; a threshold value could be determined for the microphone; or a threshold value could be determined that is based on some combination of sensor inputs. The temporal position of the maximum absolute value of each sensor signal was located. The located temporal position was not always the same from one sensor to another. An event window of data values was defined for each sensor stream balanced around the maximum point, having a time period of 0.5 seconds. As will be appreciated and understood, the event window may capture a wider or narrower time period depending on the specific implementation and the type of gesture being detected (e.g. swipes may have a wider event window time period compared to taps). If the temporal position of the maximum absolute value for a sensor was too close to the edge of the gesture detection window, the event window was extracted from the previous or next gesture detection window. The event windows for each sensor identified in step (1) proceed to step (2) gesture classification 730.

For the example implementation utilizing the Moto 360, during step (1) gesture event detection 720, data was segmented by applying a Hamming window (n=62) to the z-axis of the gyroscope data, and peak detection is performed. As will be appreciated and understood, a variety of signal processing window functions having a variety of shapes and sample sizes could be applied. In the example implementation, once a peak in the gyroscope data was recognized, the peak marked the center of a 1-second frame of data, or event window, for each sensor. The data from each event window for each sensor then proceeded to step (2) gesture classification 730.

As will be appreciated and understood, according to some embodiments, a sliding window approach, including a sliding window approach that applies a Hamming window or other signal processing window may be applied in real time to streaming data. Gesture detection and gesture classification may be performed by a processor on a wearable electronic device. Alternatively, the wearable electronic device may be paired with or otherwise in communication with an external computing device that may perform gesture detection and gesture classification or some computational portion thereof. In the example implementations described herein utilizing the SmartWatch3 and Moto 360, two to three seconds of data were recorded from each sensor for each gesture for offline analysis.

According to some embodiments, during step (2) gesture classification 730, features can be calculated for each event window to generate an event vector. An event vector can be compared to models representing gesture events. Based on the event vector's fit with models representing gesture events, the event vector can be classified as representing a gesture.

In the example implementations, features were calculated for each event window for each sensor and incorporated into an event vector. For implementations utilizing the SmartWatch3, a collective total of 286 features were calculated utilizing event window data from each of the three sensors as follows. For each axis of the linear acceleration and rotational movement, virtual sensors were derived by taking the derivative of the data for each axis; then for each axis of the raw sensor and virtual sensors, a set of statistical features were extracted including maximum, minimum, mean, median, standard deviation, root-mean-square, variance, zero-crossing rate, and values of peaks and their differences. To capture the relationship between the different axes of each IMU sensor, the ratio and differences of the energy and first and second absolute peak values of each two axes on each sensor were calculated. A 50 point Fast Fourier Transform (FFT) was performed on the rotational movement data from the gyroscope, resulting in 24 features (abandoned first bin to eliminate constant energy across the frequency spectrum) for each axis. The resulting 24 features represent an energy spectrum across frequencies that can be used in gesture classification. Since the frequency of example gesture families utilized in the example implementations are under 6 kHz, only the values of the first three bins of the FFT results and the entropy across the values of different bins are added into an event vector.

As would be appreciated and understood, various combinations of statistical features calculated based on data from the IMU, including additional, alternative, or fewer features, could be incorporated into the event vector. Further, mathematical methods for calculating the features are not limited to the above-described FFT.

Continuing with calculation of features for implementations utilizing the SmartWatch3, for acoustic data, the event data window was divided into frames of 30 ms with 50% overlap. FFT is performed on the acoustic data frames, and FFT results are averaged, keeping only the first 30 values of the FFT results representing frequencies between 0 Hz and 500 Hz. The center of mass across the frequencies is added to the feature vector. As would be appreciated and understood, the event window for acoustic data could be divided in to acoustic data frames of wider or narrower duration, and the FFT could be performed to capture a wider or narrower range of frequencies. Mel-frequency cepstral coefficients (MFCC) of the acoustic data were also utilized as features of the event vector.

As would be appreciated and understood, any statistically relevant parameters correlating to a gestures in a gesture family that facilitate identifying or classifying gesture events could be incorporated into the event vector.

For implementations utilizing the Moto 360, a collective total of 200 features were calculated utilizing event window data from each of the three sensors as follows. Eight statistical features (maximum, minimum, mean, standard deviation, root-mean-square, variance, and zero-crossing counts) were calculated for each axis of linear acceleration and rotational movement. A 50 point FFT was performed on the rotational movement data from the gyroscope, resulting in 24 features (first bin abandoned) for each axis. Frames of 30 ms with 50% overlap were extracted from acoustic data and FFT was performed on the acoustic data frames. Values of the same bin were added across different acoustic data frames in the same event window to construct acoustic data FFT results. The values of the lower 35 bins (0 Hz to 560 Hz), the values of the higher 15 bins (3760 Hz to 4000 Hz), and the fundamental frequency were taken by calculating the center of mass of the FFT results. MFCC of the acoustic data were also utilized as features of the event vector.

According to some embodiments, models representing gesture events can be created by using event vectors to train a classifier to recognize which gesture has been performed. For the example implementations utilizing the SmartWatch3 and the Moto 360, each event vector was compared to a set of data models using a Support Vector Machine (SVM) to classify the data from the associated event windows as a modeled gesture. In the example implementations, sequential minimal optimization (SMO) of SVM provided by Weka was used for building data models and for gesture classification. As would be appreciated and understood, embodiments are not limited to utilizing a SVM as a classifier, and any classifier that can be trained could be utilized to classify gesture events.

4. Demonstrations—User Trials

For SmartWatch3 implementation evaluation, twelve participants (6 male and 6 female with an average age 26 of years) from the Georgia Institute of Technology campus provided user study data as follows. The study was conducted in an open space at a university building, where the sound from the air conditioner as well as talking and movement could be heard. Participants were asked to wear the watch on the left wrist and use the right hand to perform the gesture. Participants were advised to wear the watch closer to the hand and adjust the band tightly but comfortably on the wrist. For consistency and helping participants remember the locations of each tap gesture, a number pad as depicted in FIG. 1 and FIG. 2A was drawn on the back of each participant's hand.

A researcher then demonstrated the entire gesture family, including ten tap locations in the keypad region 110 and one tap in the one touch region 105, and asked the participant to practice. The formal study consisted of 8 sessions per participant. During each session, the participant performed all the gestures while sitting in front of a table, where they could rest their elbow during the study. The participants were asked to take breaks for a few minutes between sessions to reduce fatigue. During these breaks, participants could walk around or take the watch off if desired. Each session lasted approximately 45 minutes on average.

During each session, participants were asked to follow the stimuli displayed on the screen of the watch to perform the NumPad 110a tap gestures. The sequence of the stimuli was randomized. Video of the sessions were recorded. Five instances of each gesture were collected per session. Over eight sessions with twelve participants, data was collected from 5,280 total gestures. Data from each gesture event was saved into a 2-second raw data file for further analysis. Sixteen gesture event data files corresponding to instance where the researcher observed the participant tapping at the wrong position or missing the event stimulus were not included in the analysis described below.

To understand how the system works when the training data came from different sessions, a "leave-one-session-out" method was used to evaluate the system. For each participant, the gesture instances from one session were used as the testing data, and instances from the remaining seven sessions were used as the training data to build the model. This step was repeated eight times for each participant.

If during step (1) gesture event detection 720, a gesture event was not detected in a gesture event data file this gesture event counted as a false negative error. If, during step (1), more than one gesture event was identified in a gesture event data file, this gesture event counted as a false positive error. Data files of gesture events that counted as false negative or false positive did not proceed to step (2) gesture classification 730. The observed false positive rates were approximately 0.2%, and the observed false negative rates were approximately 3% for NumPad, DPad and CornerPad.

For NumPad testing, 9 false positive and 162 false negative errors were observed. Of the 162 false negative errors, 13 of the false errors were caused because the magnitude of the rotational movement and acceleration data did not exceed the pre-defined data thresholds for step (1) gesture event detection 720. The remaining 149 false negative errors occurred because the actual timing of the user's gesture input was incompletely captured or absent from the gesture event window. The cause of these false negative errors had three primary reasons: the participant made weak taps, the participant performed gestures either too early to too late such that only part of the user's gesture input fell within the 2 second recorded window, or recorded audio data was not synchronized to the IMU data when saving the 2 second recorded window resulting in the audio file not containing the entire gesture. Acoustic data misalignment was observed to occur more often when the smart watch became over heated after performing the heavy computing workload for a certain period of time. As the smart watches and wearable electronic devices become more powerful in the future, it is reasonable to expect the last two kinds of false negative errors can be avoided by running the whole system on-line exclusively on the watch.

During gesture classification, the collective average accuracy across 12 users for each touch position on NumPad 110a in the leave-one-session-out evaluation was 91% with accuracies ranging from 95% for the highest accuracy participant to 82% for the lowest accuracy participant. Recorded video of the lowest accuracy participant indicated that the participant performed the tap gesture lighter than other participants. Microphone data from the lowest accuracy participant barely captured the sound of some gesture events, likely contributing to the lower observed accuracy.

Comparing tap locations, the lowest precision of 86% was provided by number 8 on NumPad 110a, with higher confusion existing between adjacent tap locations. For instance, 3% and 7% of the instances of taps to 8 were miss-classified as 7 and 9 respectively. Taps to 0 and to the one touch region 105 were the most accurate gestures at 97% accuracy, each. The positions of these two gestures are distinct from others, possibly contributing to the higher accuracy. Closely spaced, adjacent tap locations were observed to have more similar displacement patterns during a gesture event compared to tap locations spaced further apart.

In some example embodiments, and in the example implementation, the DPad 110b gesture family is a subset of the NumPad 110a gestures, utilizing taps at the number 2, 4, 6, and 8 positions. The average accuracy for DPad across 12 participants was 97% with the accuracies ranging from 99% for the highest accuracy participant to 91% for the lowest accuracy participant. Taps to the number 4 provided the lowest accuracy (97%) and taps to the one touch region 105 provided the highest accuracy (98%).

In some example embodiments, and in the example implementation, the CornerPad 110c gesture family is a subset of the NumPad gestures, utilizing taps at the number 1, 3, 7, and 9 positions. The average accuracy for CornerPad across 12 participants was 97% with accuracies ranging from 99% for the highest accuracy participant to 91% for the lowest accuracy participant. Taps to the number 7 provided the lowest accuracy (94%) and taps to the number 9 provided the highest accuracy (99%).

The results of leave-one-session-out validation provide a good estimate of how well the example gesture classifier can perform on recognizing different gestures across different sessions for a given participant. Further experiments were conducted with the dataset collected from the 12 participants to explore the effectiveness of user-dependent, user-independent, and user-adaptive gesture models.

User-dependent models only use the data from the same participant to train a model which will be then used for classifying his/her own gestures. Usually, a model trained with more training gesture events provide higher recognition accuracies, but also require longer time to collect the data from the participant, which can be annoying. To investigate how many training gesture events may be effective for training a user-dependent model, the first 5, 10, 15, and 20 collected gesture events per gesture from a given participant were used to train four separate SVM models. Remaining gesture events of that participant were used to test each of the four models. When only using 5 gesture events to build a model, the overall accuracies for NumPad, DPad and CornerPad across 12 participants were 71%, 89% and 86%. The highest accuracies were 87%, 97%, and 95% respectively for NumPad, DPad and CornerPad, when the user-dependent models were trained with 20 gesture events per gesture for each participant. In practice, according to some embodiments, a user can provide training data in a small number of sessions, which can be used to build gesture classification models for use in later user sessions.

Compared with user-dependent models, user-independent models (leave-one-user-out) do not require a user to provide any training data before using the technique. User experience may be improved by reducing the workload on the side of the user; however, user-independent gesture models would need to be initially built with a higher standard of reliability.

In the example implementation, a SVM was trained with the data of 11 participants from the total 12 participants, and the data from the remaining participant was tested. The average accuracy across 12 participants for the NumPad, DPad and CornerPad were 69%, 85% and 90% respectively.

The user-adaptive model falls in between the user-independent and user-dependent models, considering the amount of effort required for each user to provide training instances. The user-adaptive model may strengthen user-independent models by adding a few instances per gesture from an individual user. In the example implementation, user-adaptive models were generated by incrementally adding 5, 10, 15, and 20 gesture events per gesture from each participant to the user-independent training set. Accuracies of the user-adaptive model increased over the accuracy of the user-independent model as more personalization data was added to the models. The highest accuracies were reached when 20 instances were added to the models, which were 81%, 93%, and 96% for NumPad, DPad and CornerPad respectively.

Observed accuracies of user-adaptive models with 20 instances per gesture were lower than the accuracies of user-dependent models built with similar number of training instances. This may be due to tap locations being different from person to person based on different hand sizes. Adding more training data from others may not necessarily help improve the recognition accuracy.

User-independent models may be effective for a smaller gesture sets. In the example implementation, CornerPad achieved 90% accuracy with user-independent models. With 5 and 10 instances added in user-adaptive models for CornerPad 110*c*, the accuracy further increased to 93% and 95% respectively. The tapping locations in CornerPad 110*c* were spaced wider compared to the tapping locations in DPad 110*b* and NumPad 110*a*, which potentially provided more distinguishable characteristics in different gestures. One approach could be to ask the user to test each gesture before using it and only provide a few calibration gestures for those gestures that may be misclassified.

Data collected as described above using the SmartWatch3 was additionally evaluated to determine the accuracy of gesture detection using only the data from IMU or the microphone in a traditional 10-fold-cross-validation for the NumPad 110*a* gesture set (FIG. 2A) on each participant. Accuracies for IMU data only, acoustic data only, and IMU plus acoustic data were 89%, 66%, and 93% respectively.

For the Moto 360 implementation evaluation, one researcher provided user study data as follows. The researcher collected approximately 60 instances for each gesture to build gesture recognition models for gesture families that include a single tap to the one touch region 105, taps to each of the ten locations on the NumPad 110*a* in the keypad region 110 and four swipe gestures 110*d* in the keypad region 110 for a total of 15 distinct gestures. A number pad as shown in FIG. 1 was drawn on the back skin of the researcher's left hand for a week; data was collected during six sessions over the course of the week; and the researcher performed each of the 15 distinct gestures ten times per session.

A SVM model based on user data was evaluated by 10-fold-cross-validations. The accuracies for all 15 gestures were between 90% and 97%. The cross-validation results indicated that the 15 on-skin gestures are recognizable. Low confusion was observed between slides versus taps. One tap in the one touch region 105 provided the highest precision (100%) and recall (98%), indicating this gesture may be a good candidate for gesture commands that require a high accuracy (e.g. delete or activate). The number 9 provided the lowest accuracy (83%), being confused most frequently with the number 6.

Data collected as described above using the SmartWatch3 was additionally evaluated to determine the accuracy of gesture detection using only the data from IMU or the microphone in a traditional 10-fold-cross-validation for the NumPad 110*a* gesture set (FIG. 2A) on each participant. Accuracies for IMU data only, acoustic data only, and IMU plus acoustic data were 55%, 83%, and 91% respectively. Using data from all three sensors, but removing features derived from the frequencies of the acoustic spectrum from the event vectors, resulted in an accuracy of 86%. Using data from all three sensors, but removing MFCC features of the acoustic data resulted in an accuracy of 85%.

In contrast to results described in relation to the SmartWatch3 above, a similar analysis of data collected during the example implementation of the Moto 360 suggests that acoustic data may be more informative in classifying gestures compared to IMU data. In agreement with evaluation of the SmartWatch3, evaluation of the Moto 360 suggests that using data from the microphone and the IMU may significantly increase gesture recognition over IMU only or microphone only.

5. Other Considerations

As will be appreciated and understood, the above-described implementations demonstrate certain aspects of embodiments of the present disclosure, but embodiments differ from these example implementations while staying within the scope of the present disclosure. For example, certain embodiments may be designed with additional real-world application considerations in mind.

False positive errors can be frustrating to a user, resulting in unwanted user commands, such as placing a phone call. According to some embodiments, more advanced signal processing techniques such as band-pass filtering, may be utilized to filter out noise in noisy environments. Additional criteria could be applied during the gesture event detection step utilizing collected noise data to reduce false positives due to high volume ambient noise. According to some embodiments, an activation gesture could be required before inputting data through the body. The activation gesture can be intuitive to perform and can preferably have less confusion with other gestures in addition to providing low FN and FP error rates. For example, for embodiments incorporating a smart watch as a wearable electronic device 100, a single tap or double tap in the one touch region 105 may be used as an activation gesture.

A few example gesture sets are tested as described above; however, other gesture sets could be utilized. One challenge is to design a gesture set that is both memorable as well as machine recognizable. One way to enhance gesture recognition is to provide a small set of tap gestures, which are located at greater distances between each other (e.g., DPad, CornerPad). Therefore, the user can easily memorize the location of each tap gesture. A drawing layout may not be needed in such a case. Since there is a larger space between the two tap locations, variance between different taps for the same gesture can be tolerated by the system and used for recognition.

According to some embodiments, another method to prevent drawing icons on the skin is to utilize the natural layout of the hand and map gestures to different parts of the body. For instance, each hand consists of 4 knuckles. According to some embodiments, knuckle may be mapped with a tap gesture, so that a user can easily repeat the tap even without any marker on the skin. According to some embodiments, a projection onto the body may be utilized to mark gesture locations.

However, painting on the hand may not always be unacceptable for some users, if the drawn picture is well designed. For instance, many people have already a tattoo on their skin. According to some embodiments a gesture family may be designed to be compatible with a tattoo or tattoo-like drawing, such that people will not feel uncomfortable with a "Tattoo" style layout on their skin.

In implementations described above, gesture instances were collected while the participants were holding their arms in a static position. As will be appreciated and understood embodiments are not limited to use under the narrow test conditions described above. In practical scenarios, users may use some embodiments while in motion (e.g., while walking). Tapping on the body in motion would influence the inertial signals, as well as potentially the accuracy of the tapping locations. According to some embodiments, referring to FIG. 7, context detection may be used during gesture event detection 720 to either prevent sensor data generated by a walking motion or other contextual influence from progressing to gesture classification 730, or to process the sensor signal by filtering or other means to compensate for contextual influences before performing gesture classification 730 on the sensor signals. Context detection can be accomplished by utilizing separate gesture classification models when the user is in motion (or different states of motion, such as stationary, walking or running). In such embodiments, to classify a gesture, the user's motion state or other context data can first be classified (for example, using something like Google's Activity Recognition service), then the appropriate thresholds and models could be utilized during gesture event detection to account for the user's state of motion or other context data. According to some embodiments, to reduce the potential false positive errors while the user is in motion, a high-pass filter can be applied to the IMU data to remove the low-frequency motion (such as walking). The sound generated by a gesture event such as tapping may change in different situations for a given participant. For instance, if the hands sweat or are otherwise moistened, the wet skin may change the acoustic signature of the gesture, potentially providing an unknown influence on the system's performance. Clothing covering the skin, such as a sleeve covering the one touch region 105 of the arm, or gloves on either the tapping or receiving hand may not fit gesture recognition models based on skin-to-skin contact. As will be appreciated and understood, taps and other gestures may be detected by the IMU and the microphone of the wearable electronic device even when clothing prevents direct skin-to-skin so long as the gestures result in motion of the wearable electronic device detectable by the IMU and sound detectable by the microphone. According to some embodiments, additional gesture recognition models may be utilized to detect and classify scenarios where clothing interrupts direct skin-to-skin contact.

Although the present disclosure has generally discussed embodiments related to wearable electronic devices such as a smart watch, it will be understood that certain aspects of the disclosed technology may be implemented using or with a non-wearable or optionally wearable portable electronic devices. For example, a smart phone may be held in the hand of a user. While held in the hand, the user may perform gestures on their body in the vicinity of the smart phone (e.g., on their fingers, wrist, forearm, or hand). The smart phone may be configured to capture sensor data from one or more sensors integral to the smart phone and respond to gesture, in response to an analysis of the sensor data indicating that the contact corresponds to the gesture. Again, this is merely an example, and aspects of the present disclosure may be implemented in a variety of portable electronic devices.

What is claimed is:

1. A wearable electronic device comprising:
   one or more sensors;
   a microprocessor; and
   memory having stored thereon instructions that, when executed by the microprocessor, are configured to:
   capture, in response to a contact to a body of a user in a vicinity of the wearable electronic, sensor data from one or more of the sensors;
   analyze at least a portion of the sensor data comprising:
   performing gesture event detection that includes a walking motion of the user; and
   compensating for an effect of the walking motion on the sensor data; and
   provide, in response to analyzing at least a portion of the sensor data indicating that the contact corresponds to a first gesture, a first command to the microprocessor;
   wherein the sensor data includes an acceleration signal, a rotational movement signal, and an acoustic waveform signal.

2. The wearable electronic device of claim 1, wherein the wearable electronic device is a wrist-mounted device.

3. The wearable electronic device of claim 2, wherein the first gesture is a tap or a swipe performed on a hand or forearm of the user.

4. The wearable electronic device of claim 1, wherein the instructions, when executed by the microprocessor, are further configured to
   capture, in response to a second contact with the user, second sensor data from one or more of the sensors; and
   provide, in response to an analysis of at least a portion of the second sensor data indicating that the second contact corresponds to a second gesture, a second command to the microprocessor.

5. The wearable electronic device of claim 4, wherein the first command and the second command are distinct commands mapped to the first gesture and the second gesture, respectively.

6. The wearable electronic device of claim 1, wherein the first command executed by the microprocessor controls the wearable electronic device to respond to the first gesture by providing a feedback to the user.

7. The wearable electronic device of claim 1, wherein the first gesture is part of a gesture family; and wherein the gesture family comprises at least ten gestures.

8. The wearable electronic device of claim 1, wherein the first gesture comprises a tap to a back of a forearm of the user.

9. The wearable electronic device of claim 1, wherein the instructions, when executed by the microprocessor, are further configured to:
capture, in response to a second contact with the user, second sensor data from one or more of the sensors; and
provide, in response to an analysis of at least a portion of the second sensor data indicating that the second contact does not correspond to a gesture in a gesture family in which the first gesture is a part, a second command to the microprocessor that the second contact does not correspond to a gesture in the gesture family detectable by the wearable electronic device.

10. A wearable electronic device comprising:
sensors;
a microprocessor; and
a memory having stored thereon instructions that, when executed by the microprocessor, are configured to:
capture, in response to a contact to a user of the wearable electronic device, sensor data from one or more of the sensors;
analyze at least a portion of the sensor data;
extract features from at least a portion of the sensor data; and
provide, in response to analyzing at least a portion of the sensor data indicating that the contact corresponds to a gesture, a command to the microprocessor;
wherein the sensor data includes at least acceleration data, rotational movement data, and acoustic waveform data; and
wherein extracting the features from at least a portion of the sensor data comprises:
performing a time-based derivative and calculating statistical parameters of the acceleration data;
Performing a Fast Fourier Transform on the rotational movement data; and
performing a Fast Fourier Transform on the acoustic waveform data.

11. The wearable electronic device of claim 10, wherein the acceleration data is from an accelerometer;
wherein the rotational movement data is from a gyroscope; and
wherein the acoustic waveform data is from a microphone.

12. The wearable electronic device of claim 10, wherein the gesture is part of a gesture family; and
wherein the command instructs the microprocessor to begin or cease monitoring for a different gesture in the gesture family;
wherein each gesture in the gesture family is mapped to one of a plurality of commands; and
wherein the command is one of the plurality of commands.

13. A method comprising:
capturing, in response to a contact to a body of a user in a vicinity of a wearable electronic device, sensor data from one or more sensors of the wearable electronic device;
analyzing the sensor data; and
providing, in response to analyzing the sensor data indicating that the contact corresponds to a gesture in a gesture family, a command to a microprocessor of the wearable electronic device;
wherein analyzing the sensor data comprises:
performing gesture event detection; and
performing gesture classification;
wherein performing gesture event detection comprises:
determining a walking motion of the user; and
compensating for an effect of the walking motion on the sensor data; and
wherein the sensor data includes at least acceleration data, rotational movement data, and acoustic waveform data.

14. The method of claim 13, wherein performing gesture classification comprises:
extracting features from the sensor data;
generating an event vector based on at least a portion of the features; and
comparing the event vector to gesture classification models.

15. The method of claim 14, wherein the gesture classification models comprise user-independent models.

16. The method of claim 14, wherein the gesture classification models are based, at least in part, on contacts to the body; and
wherein each of the contacts correspond to a gesture in the gesture family.

17. The method of claim 16, wherein gestures in the gesture family represent at least a ten-key number pad.

18. The method of claim 13, wherein the gesture is selected from the group consisting of a tap, a swipe, and a double tap.

19. The method of claim 13 further comprising providing, based on the command provided to the microprocessor, feedback to the user.

20. The method of claim 19, wherein the feedback to the user is selected from the group consisting of a text or number entry displayed on a screen of the wearable electronic device, a selection of a menu item displayed on the screen, and the selection of a button displayed on the screen.

21. A non-transitory computer readable medium having stored thereon computer program code that, when executed by a processor, controls a processor to perform a method according to claim 13.

22. A method comprising:
capturing, in response to a contact to a user of a wearable electronic device, sensor data from one or more sensors of the wearable electronic device;
analyzing at least a portion of the sensor data;
extracting features from at least a portion of the sensor data; and
providing, in response to analyzing at least a portion of the sensor data indicating that the contact corresponds to a gesture, a command to a microprocessor of the wearable electronic device;
wherein the sensor data includes at least acceleration data, rotational movement data, and acoustic waveform data; and
wherein extracting the features from at least a portion of the sensor data comprises:
performing a time-based derivative and calculating statistical parameters of the acceleration data;
performing a Fast Fourier Transform on the rotational movement data; and
performing a Fast Fourier Transform on the acoustic waveform data.

23. The method of claim 22 further comprising generating an event vector based on at least a portion of the features.

24. The method of claim 23 further comprising comparing the event vector to gesture classification models.

25. The method of claim 22, wherein the gesture is a member of a gesture family; and wherein the gesture family includes ten gestures corresponding to a number pad on a back of a hand of the user.

26. The method of claim 22, wherein the gesture comprises a tap to a back of a forearm of the user;
wherein the gesture is a member of a gesture family; and
wherein the command instructs the microprocessor to begin or cease monitoring for one or more other gestures in the gesture family.

27. The method of claim 22, wherein analyzing at least a portion of the sensor data comprises performing gesture event detection comprising determining an event window that includes gesture event data.

28. A non-transitory computer readable medium having stored thereon computer program code that, when executed by a processor, controls a processor to perform a method according to claim 22.

29. A method comprising:
capturing, in response to a contact to a body of a user in a vicinity of a portable electronic device, sensor data from one or more sensors of the portable electronic device;
analyzing at least a portion of the sensor data comprising:
performing gesture event detection that includes a walking motion of the user; and
compensating for an effect of the walking motion on the sensor data; and
providing, in response to analyzing at least a portion of the sensor data indicating that the contact corresponds to a first gesture, a first command to a microprocessor of the portable electronic device;
wherein the sensor data includes an acceleration signal, a rotational movement signal, and an acoustic waveform signal.

30. The method of claim 29, wherein analyzing at least a portion of the sensor data further comprises performing gesture classification.

31. The method of claim 29, wherein gesture event detection further includes comparing a peak value from the sensor data to a threshold value.

32. The method of claim 29, wherein gesture classification includes extracting a plurality of features from the sensor data, generating an event vector based on the plurality of features, and comparing the event vector to a plurality of gesture classification models; and
wherein the plurality of gesture classification models comprise user-independent models.

33. The method of claim 32, wherein the plurality of gesture classification models are based, at least in part, on a plurality of contacts to the body of the user in the vicinity of the portable electronic device, each of the plurality of contacts corresponding to one of a plurality of gestures in a gesture family.

34. The method of claim 33, wherein the plurality of gestures in the gesture family represents a ten-key number pad.

35. The method of claim 29 further comprising extracting a plurality of features from the sensor data.

36. The method of claim 35, wherein the extracting of the plurality of features includes performing a time-based derivative and calculating statistical parameters of the acceleration signal, performing a Fast Fourier Transform on the rotational movement signal, and performing a Fast Fourier Transform on the acoustic waveform signal.

37. The method of claim 35 further comprising generating an event vector based on the plurality of features.

38. The method of claim 37 further comprising comparing the event vector to a plurality of gesture classification models.

39. The method of claim 29, wherein the first gesture is a tap, a swipe, or a double tap.

40. The method of claim 29, wherein the first gesture is one of a plurality of gestures in a gesture family, wherein each of the plurality of gestures in the gesture family is mapped to one of a plurality of commands, and wherein the first command is one of the plurality of commands.

41. The method of claim 40, wherein the portable electronic device is configurable to be held in a hand of the user and the contact to the body is in the vicinity of the hand of the user.

42. The method of claim 41, wherein the contact is a tap, a swipe, or a double tap of a finger to the back of a hand or a forearm.

43. The method of claim 42, wherein the contact is direct skin-to-skin contact.

44. The method of claim 41, wherein the gesture family includes ten gestures corresponding to a number pad on the back of the hand.

45. The method of claim 41, wherein the first gesture comprises a tap to a forearm of a same arm attached to the hand of the user holding the portable electronic device, and wherein the first command instructs the microprocessor to begin or cease monitoring for one or more other gestures in the gesture family.

46. The method of claim 29 further comprising providing, based on the first command provided to the microprocessor, feedback to the user.

47. The method of claim 46, wherein feedback to the user includes a text or number entry displayed on a screen of the portable electronic device, a selection of a menu item displayed on the screen, or the selection of a button displayed on the screen.

48. The method of claim 29 further comprising:
capturing second sensor data from one or more sensors of the portable electronic device; and
determining that the second sensor data does not correspond to a gesture in a gesture family detectable by the portable electronic device.

49. A non-transitory computer readable medium having stored thereon computer program code that, when executed by a processor, controls a processor to perform a method according to claim 29.

* * * * *